(12) United States Patent
Cardona Iglesias et al.

(10) Patent No.: US 8,795,719 B2
(45) Date of Patent: Aug. 5, 2014

(54) IMMUNOTHERAPEUTIC AGENT SUITABLE FOR THE PRIMARY PROPHYLAXIS OF TUBERCULOSIS

(75) Inventors: Pere Joan Cardona Iglesias, Barcelona (ES); Isabel Amat Riera, Barcelona (ES)

(73) Assignee: Archivel Farma, S.L., Badalona (Barcelona) (ES)

( * ) Notice: Subject to any disclaimer, the term of this patent is extended or adjusted under 35 U.S.C. 154(b) by 625 days.

(21) Appl. No.: 13/120,476

(22) PCT Filed: Sep. 3, 2009

(86) PCT No.: PCT/ES2009/000436
§ 371 (c)(1),
(2), (4) Date: Jun. 7, 2011

(87) PCT Pub. No.: WO2010/031883
PCT Pub. Date: Mar. 25, 2010

(65) Prior Publication Data
US 2011/0268788 A1    Nov. 3, 2011

(30) Foreign Application Priority Data
Sep. 19, 2008   (ES) .................................. 200802657

(51) Int. Cl.
*A61K 39/00*    (2006.01)
*A61K 39/04*    (2006.01)

(52) U.S. Cl.
USPC ...................................... 424/450; 424/234.1

(58) Field of Classification Search
CPC .............................. A61K 39/00; A61K 39/04
See application file for complete search history.

(56) References Cited

U.S. PATENT DOCUMENTS

| | | | | |
|---|---|---|---|---|
| 3,529,057 | A * | 9/1970 | Misaki et al. | 424/282.1 |
| 6,982,085 | B2 * | 1/2006 | Andersen et al. | 424/190.1 |
| 7,566,459 | B2 * | 7/2009 | Ernst et al. | 424/248.1 |
| 8,076,469 | B2 * | 12/2011 | Andersen et al. | 536/23.7 |
| 8,246,944 | B2 * | 8/2012 | Cardona Iglesias et al. | 424/93.1 |
| 2001/0038858 | A1 * | 11/2001 | Roser et al. | 424/488 |
| 2003/0165525 | A1 * | 9/2003 | Andersen et al. | 424/190.1 |
| 2004/0180056 | A1 * | 9/2004 | Orme et al. | 424/184.1 |
| 2005/0106107 | A1 * | 5/2005 | Nakamura | 424/9.8 |
| 2007/0026020 | A1 * | 2/2007 | Ernst et al. | 424/248.1 |
| 2007/0041997 | A1 * | 2/2007 | Finlay et al. | 424/200.1 |
| 2008/0267990 | A1 * | 10/2008 | Andersen et al. | 424/190.1 |
| 2010/0068258 | A1 * | 3/2010 | Cardona Iglesias et al. | 424/450 |
| 2010/0172845 | A1 * | 7/2010 | Stoops et al. | 424/45 |

FOREIGN PATENT DOCUMENTS

| | | | | |
|---|---|---|---|---|
| ES | 2 231 037 | | 5/2005 | |
| WO | 00/66157 | * | 11/2000 | ............. A61K 39/00 |
| WO | WO 03/004520 A2 | | 1/2003 | |
| WO | WO 2005/042013 A1 | | 5/2005 | |
| WO | 2008/053055 | * | 5/2008 | ............. A61K 30/04 |
| WO | WO 2008/053055 A1 | | 5/2008 | |

OTHER PUBLICATIONS

P9w1g7-Unitprot accession number, pp. 1-4, Apr. 16, 2014.*
I6yhc7-Uniprot accession number, pp. 1-5, Oct. 3, 2012.*
Agger, et al., "Specific Acquired Resistance in Mice Immunized with Killed Mycobacteria," Scand. J. Immunol. 56, 443-447, 2002.
International Search Report for PCT International Application No. PCT/ES2009/000436 mailed Jan. 29, 2010.

* cited by examiner

*Primary Examiner* — Albert Navarro
*Assistant Examiner* — Ginny Portner
(74) *Attorney, Agent, or Firm* — RatnerPrestia

(57) ABSTRACT

The present invention relates to the use of an immunotherapeutic agent having cell wall fragments of a virulent strain of *Mycobacterium tuberculosis* for the preparation of a drug suitable for the primary prophylaxis of tuberculosis. The immunotherapeutic agent is capable of inducing a protective response that is more effective than the conventional BCG vaccine and reduces the number of viable bacilli in the lungs and in the spleen of individuals recently infected by *M. tuberculosis*.

14 Claims, No Drawings

IMMUNOTHERAPEUTIC AGENT SUITABLE FOR THE PRIMARY PROPHYLAXIS OF TUBERCULOSIS

This application is a U.S. National Phase Application of PCT International Application No. PCT/ES2009/000436, filed Sep. 3, 2009.

FIELD OF THE ART

The present invention relates to the use of an immunotherapeutic agent based on cell wall fragments of a virulent strain of *Mycobacterium tuberculosis*-complex for the preparation of a drug suitable for the primary prophylaxis of tuberculosis.

STATE OF THE PRIOR ART

Tuberculosis is a chronic infectious disease caused by the *Mycobacterium tuberculosis*-complex (MTB-C) bacilli, which currently include the species *M. tuberculosis, M. bovis, M. microti* and *M. africanum.*

According to the World Health Organization's 2008 report, 9,000,000 new cases of people manifesting the disease are recorded worldwide every year and about 2,000,000 people die. It is considered that there are more than 2,500,000,000 infected people worldwide and that 90-100 million more new infections are generated each year.

The current vaccine which is used in the preventive treatment against tuberculosis is based on bacteria of the strain called BCG (Bacillus Calmette-Guerin), an attenuated variant of *M. bovis.*

Patent application WO-A-2008/053055 discloses the use of an immunotherapeutic agent comprising cell wall fragments of a virulent strain of *Mycobacterium tuberculosis*-complex (MTB-C) for the preparation of a drug for the prophylactic treatment of tuberculosis and for preventing the infections caused by *M. tuberculosis*. Said agent is usually administered sufficiently in advance with respect to infection. Said patent application also describes that the aforementioned immunotherapeutic agent is more effective than the current vaccine based on the attenuated strain BCG.

Once the infection has started, different treatments have been disclosed in the state of the art to control the development of active tuberculosis in infected people, i.e., with latent tuberculosis infection.

For example, patent application WO-A-03/004520 discloses that to control tuberculosis in infected people, both those who have not yet developed the disease and those who have already developed it, various drugs are administered, including isoniazid, for a time period which is prolonged for several months.

Patent application ES-A-2231037 discloses the use of an immunotherapeutic agent comprising cell wall fragments of a virulent strain of *Mycobacterium tuberculosis*-complex (MTB-C) for the preparation of a drug for the treatment of tuberculosis in infected people in association with other drugs such as isoniazid and the rifampicin. Said combination increases the efficacy of the drugs since it generates an immunological response against the bacilli that are not in the active metabolism phase, which further reduces the risk of developing resistance.

The article entitled "*Documento de consenso sobre el estudio de los contactos en los pacientes tuberculosos"* by the *Grupo de Estudio de Contactos at the Unidad de Investigación en Tuberculosis de Barcelona* (UITB) published in Med. Clin. (Barc), 1999, 112, 151-156, discloses that a tuberculosis control program must first and foremost ensure the diagnosis and early treatment of the patients, assuring the correct compliance with therapy and, when suitable compliance rates are reached, the study of contacts must be further develop. The individual who has had a relationship with a tuberculosis patient is considered a "contact".

Therefore, the fact that the mechanism of transmission of the latent tuberculosis infection is by means of inhaling aerosols infected by *M. tuberculosis* means that the "contacts" from living with or frequently being around a tuberculosis patient, especially if it is pulmonary and bacilliferous tuberculosis, are a risk group that must be examined.

Therefore control of the "contacts" of a case of tuberculosis is one of the most effective activities for achieving the control of the endemic disease in community. This activity allows classifying the "contacts" into three groups:

I. Exposed but not yet infected individuals. The tuberculin skin test (TST) is negative. This person belongs to group I of the American Thoracic Society (ATS) classification. Primary prophylaxis seeks to prevent infection of individuals exposed to the contagion, and in many cases it helps avoid infection.

II. Individuals with latent tuberculosis infection but who are not sick. In other words, group II of the ATS classification. They are possibly tuberculin reaction (TST) converters with a high risk of generating the disease. Secondary prophylaxis, particularly, secondary chemoprophylaxis, considerably reduces this risk.

III. Individuals who are already sick, belong to group III of the ATS classification, usually with primary forms of the disease and therefore scarcely or not at all contagious. Chemotherapy will prevent them from becoming sources of contagion.

The primary prophylaxis of the infection that is usually administered to group I of the ATS today is actually a primary chemoprophylaxis that is based on the administration of isoniazid in doses of 5 mg/kg, not exceeding 300 mg/day and in a daily regimen. Said treatment is indicated in all individuals of any age, with negative TST, who are living with and/or in close contact with pulmonary tuberculosis patients. In this case, the primary chemoprophylaxis must be maintained for 3 months after having suspended contact with the source of infection or after the source has stopped being contagious.

The document entitled "*La Tuberculosi a Catalunya: informe*", published in 1983 by the Generalitat de Catalunya, indicated that primary chemoprophylaxis is aimed at the protection of non-infected individuals exposed to the contagion, and the purpose is to prevent the infection of the "contacts". Said treatment therefore represents a true prophylaxis of the infection and it can be affirmed that it has been openly accepted.

However, the side effects caused by primary chemoprophylaxis based on the prolonged administration of isoniazid have been disclosed in the state of the art. The article by Martinez et al., *Primary prevention and treatment of latent tuberculosis infection with isoniazid: efficacy of a control program,* 1997-2002*, Arch. Bronconeumol.,* 2005, 41(1), 27-33, discloses the problems of hepatotoxicity associated with the duration of the primary chemoprophylaxis.

Another drawback of primary chemoprophylaxis is the duration of the treatment, which can last up to 12 months. This means that the degree of compliance by the individuals who are subjected to said treatment is often unsatisfactory.

Therefore there is a need to have a primary prophylaxis of tuberculosis that has fewer side effects and is easier to comply with.

BRIEF DESCRIPTION OF THE INVENTION

The present invention is the use of an immunotherapeutic agent comprising cell wall fragments of a virulent strain of MTB-C for the preparation of a drug suitable for the primary prophylaxis of tuberculosis.

An immunotherapeutic agent comprising cell wall fragments of a virulent strain of MTB-C for being used in the primary prophylaxis of tuberculosis is also part of the object of the invention.

DETAILED DESCRIPTION OF THE INVENTION

Patent application ES2231037-A1 discloses a method for the preparation of an immunotherapeutic agent comprising cell wall fragments of a virulent strain of *Mycobacterium tuberculosis*-complex (MTB-C). It also discloses compositions containing it and the therapeutic application thereof for the combined treatment of tuberculosis in association with other drugs.

The authors of the present invention have discovered that said immunotherapeutic agent is suitable for the preparation of a drug for the primary prophylaxis of tuberculosis.

The object of the present invention is therefore the use of an immunotherapeutic agent comprising cell wall fragments of a virulent strain of *Mycobacterium tuberculosis*-complex (MTB-C) for the preparation of a drug for the primary prophylaxis of tuberculosis, wherein said agent is obtainable by a method comprising the following steps:

culturing the virulent strain of MTB-C for a time period equal to or greater than three weeks and subsequently homogenizing the cell culture in the presence of a nonionic surfactant.

An immunotherapeutic agent comprising cell wall fragments of a virulent strain of MTB-C for being used in the primary prophylaxis of tuberculosis is also part of the object of the invention, wherein said agent is obtainable by a method comprising the following steps:

culturing the virulent strain of MTB-C for a time period equal to or greater than three weeks and subsequently homogenizing the cell culture in the presence of a nonionic surfactant.

In a preferred embodiment, the method includes the following additional steps:

separating the non-fragmented cells and the solubilized components by means of centrifugation, subjecting the fraction of cell wall fragments to chemical or physical treatment to inactivate the eventual virulent strain cells that it eventually contains, and drying the obtained immunotherapeutic agent by means of lyophilization.

Primary Prophylaxis

In the context of the invention, the primary prophylaxis of tuberculosis is understood as the treatment for preventing tuberculosis infection in individuals who are exposed to the contagion and who have not tested positive in the tuberculin skin test.

The prophylactic vaccines against tuberculosis, either the vaccine based on the *Bacillus* Calmette-Guerin, or the prophylactic vaccine described in patent application WO-A-2008/053055, are administered sufficiently in advance to individuals who are not infected for preventing infections caused by *M. tuberculosis*.

The object of this invention is aimed at the use of an immunotherapeutic agent comprising cell wall fragments of a virulent strain of *Mycobacterium tuberculosis*-complex (MTB-C) for preparing a drug suitable for the primary prophylaxis of tuberculosis, which is administered to individuals who are at risk of contracting the infection through contact with infected individuals and who test negative in the tuberculin skin test.

Said individuals may have been vaccinated or not with any of the aforementioned vaccines.

In the event that the individuals have been vaccinated, the primary prophylaxis can act as an enhancer for preventing infection.

Culture of the Virulent Strain

A virulent strain of MTB-C is used in the method for obtaining the immunotherapeutic agent.

The virulent strain can be any virulent strain of MTB-C. One of the strains most used by researchers in this field is called $H_{37}Rv$ which, for example, can be freely acquired in the National Collection of Type Cultures (NCTC), London, Great Britain (accession number NC007416).

The virulent strain can be cultured by inoculation in culture media well known by the person skilled in the art, for example Middlebrook 7H10 or 7H11 agar, Sauton's medium or Proskauer-Beck medium.

The culture of the virulent strain is performed for a time period equal to or greater than three weeks, preferably comprised between 3 and 4 weeks. The temperature of the culture is preferably maintained between 34° C. and 38° C.

Once the culture has ended, the cells are isolated using techniques such as those described in patent application ES-A-2231037 for example.

Homogenization of the Cell Culture

The live cells are homogenized in the presence of a nonionic surfactant. The type of nonionic surfactant used in the homogenization process is preferably selected from the group consisting of ethoxylated alkylphenols, ethoxylated sorbitan esters, and mixtures thereof.

The nonionic surfactant is more preferably selected from the group of ethoxylated octylphenols. Ethoxylated octylphenols with an ethylene oxide content comprised between 7 and 8 moles, which are available on the market under the brand name TRITON® X-114, are more preferably used.

The nonionic surfactant content in the step of homogenization is preferably comprised between 1% and 10% by weight with respect to the total weight of the homogenate, more preferably between 3% and 6% by weight.

Said homogenization is preferably carried out in a neutral pH buffered medium, for example at a pH comprised between 6 and 8, such as that provided by PBS (phosphate-buffered saline) buffer.

Homogenization can be carried out by means of ultrasound sonication or by means of using small beads of approximately 1 mm in diameter, for example, silica or silica-zirconium beads, together with a mechanical homogenizer. A mechanical homogenizer that can be used, for example, is the Biospec Beadbeater® model.

The MTB-C cells are ruptured and small cell wall fragments are obtained by means of this homogenization process.

Separation of the Cell Wall Fragments

In a preferred embodiment the method includes a step for separating the cell wall fragments.

The homogenized mass containing the cell wall fragments is subjected to a conventional treatment to separate and reject the non-fragmented cells and the solubilized components. Centrifugation at different speeds and washing with a buffer solution as described in patent application ES-A-2231027, for example, can be done.

After performing the aforementioned purification processes, a sediment is obtained which contains the cell wall fragments which are used for preparing the drug suitable for primary prophylaxis.

Inactivation of the Cell Wall Fragments

In a preferred embodiment the sediment obtained in the previous step is dispersed in PBS buffer and subjected to a conventional treatment to assure the complete inactivation of the MTB-C cells that may have remained viable after the fragmentation and purification process.

The inactivation treatment can be a chemical process, for example by means of treatment with formol, or a physical treatment, for example by means of treatment in an autoclave or pasteurization.

Pasteurization treatment at a temperature comprised between 60° C. and 90° C., more preferably between 60° C. and 70° C., and still more preferably at a temperature of about 65° C., is preferably used.

Lyophilization of the Cell Wall Fragments

In a preferred embodiment, the dispersion of cell wall fragments in PBS buffer obtained after the inactivation treatment is lyophilized to facilitate the storage thereof. To that end, the dispersion can be distributed into vials and lyophilized by means of a conventional method at a temperature comprised between −15° C. and −25° C. and under a vacuum comprised between 0.1 and 0.5 mbar.

The vials obtained after the lyophilization process contain the immunotherapeutic agent comprising the cell wall fragments of MTB-C, and they are generally stored at very low temperatures, for example at −70° C.

Drug for the Primary Prophylaxis of Tuberculosis

As previously indicated, the object of the invention is the use of the immunotherapeutic agent comprising cell wall fragments of a virulent strain of MTB-C for the preparation of a drug suitable for the primary prophylaxis of tuberculosis.

The drug for the primary prophylactic treatment of tuberculosis comprises the immunotherapeutic agent based on cell wall fragments and, optionally, pharmaceutically acceptable diluents, adjuvants and/or excipients.

The drug can be in the form of phosphate-buffered saline solution, an aqueous solution, emulsion, or also in the form of liposomes.

The drug is preferably in the form of liposomes.

The liposomes can be formed using conventional auxiliary lipids and techniques well known by the person skilled in the art, such as those described in patent application ES-A-2231037.

The liposomes generally include phospholipids, with a neutral and/or negative net charge, and sterols.

The phospholipids used can be, for example: phosphatidylcholine, the phosphatidylserine and the phosphatidylinositol.

The majority component of the liposomes is usually phosphatidylcholine, which can be synthesized or isolated from natural sources. A commonly used commercial product is soy lecithin, which is a complex mixture of phospholipids, including phosphatidylcholine.

The sterols which are used in the preparation of liposomes can be, among others, cholesterol and the bile salts.

The liposomes are preferably formed using a mixture of soy lecithin and sodium cholate.

The liposomes can optionally contain excipients which improve their stability, such as glycine for example.

The liposomes obtained usually have a size distribution in which 99.9% are smaller than 1 micron.

The liposomes can be subjected to a conventional lyophilization process to thus obtain the immunotherapeutic agent in the form of lyophilized liposomes.

Administration of the Drug

The drug can be administered in the form of a single dose or of several doses by means of the repetition at determined time intervals. Said drug is preferably administered in the form of a single dose.

In the case of applying several doses, it is preferably to apply two doses with a time interval between them comprised between 1 and 5 weeks, preferably between 1 and 3 weeks, and still more preferably between 1 and 2 weeks.

The drug can be administered in a mucous membrane, for example, ocular, intranasal, oral, gastric, intestinal, vaginal, or in the urinary tract, or through parenteral route, for example, subcutaneous, intradermal, intramuscular, intravenous or intraperitoneal route. Administration through parenteral route is preferred.

The suitable dose depends on several parameters, including the administration route and the subject to be treated, but the dose is preferably comprised between 1 μg and 1000 μg of cell wall fragments, more preferably between 5 μg and 700 μg, and still more preferably between 5 μg and 300 μg.

The immunotherapeutic agent of the invention can be administered in combination with other drugs suitable for the primary prophylaxis of tuberculosis, simultaneously or alternately. Said drugs include isoniazid, rifampicin or other tuberculostatic agents. In the case of combined administration, the immunotherapeutic agent of the invention is administered with isoniazid.

It has surprisingly been found that the administration of the drug comprising the immunotherapeutic agent containing cell wall fragments of a virulent strain of MTB-C is suitable as a primary prophylaxis of tuberculosis in recently infected mice because it induces a protective response that is more effective than the conventional BCG vaccine in said mice.

This result is surprising in that the conventional BCG vaccine and the immunotherapeutic agent containing cell wall fragments have a substantially identical immunoprotective behavior when they are administered as a prophylactic vaccine sufficiently in advance with respect to infection, as disclosed in patent application WO-A-2008/053055.

However, the experimental results included in this description show the difference between both drugs when used in the primary prophylaxis of tuberculosis for the purpose of preventing infection due to contacts in individuals who are not infected but have been exposed to the contagion.

As is described in the Examples, four groups of mice were infected with the virulent strain $H_{37}Rv$. A few days after infection, a dose of said immunotherapeutic agent was administered to one group, two doses of the same agent separated by a one-week interval were administered to a second group, and a dose of the conventional BCG vaccine was administered to a third group. The fourth group was the control group and no drug was administered to them.

Three weeks after infection, the animals were sacrificed and the number of viable bacilli present in the lungs and in the spleen of the mice was determined. It was observed that the number of viable bacilli present in the lungs of the mice to which said immunotherapeutic agent had been administered was less than the number of viable bacilli present in the control mice group and less than that of the mice vaccinated with the conventional BCG vaccine. Particularly, the mice to which two doses of immunotherapeutic agent in the form of liposomes were administered presented the lowest number of viable bacilli of all the groups.

Although the differences among the groups of mice concerning the spleen were not statistically significant, it should be pointed out that the administration of the immunotherapeutic agent in the form of liposomes reduced the *bacillus* concentration to the point that the *bacillus* population in the group treated with two doses of the agent was eradicated (CFU=0) in 4 out of 14 cases, hence the high standard deviation detected.

Therefore, the primary prophylaxis with the immunotherapeutic agent based on cell wall fragments of a virulent strain of MTB-C protects individuals against recent infections caused by *M. tuberculosis* because it generates a protective response, in contrast with the conventional BCG vaccine which is shown to be substantially less effective.

The following example is provided for the purpose of giving the person skilled in the art a detailed explanation of specific embodiments in the invention.

Example 1

Effectiveness of the Immunotherapeutic Agent as a Primary Prophylaxis Against Infection Caused by *M. Tuberculosis*

The immunotherapeutic agent used in this example was prepared according to the method described in Example 2 of patent application ES-A-2231037.

The effectiveness of the immunotherapeutic agent based on cell wall fragments of a virulent strain of MTB-C was assayed in C57BL/6 type female mice from 6 to 8 weeks of age and free of specific pathogens.

The mice were divided into four groups of 14 animals each and were subjected to the following vaccination protocol:

1) No vaccination (control group),

2) Subcutaneously inoculated with a dose of 260 μg of cell wall fragments in the form of liposomes obtained in Example 2 of patent application ES-A-2231037 4 days after the infection of the mice by means of aerosol.

3) Subcutaneously inoculated with two doses of 260 μg of cell wall fragments in the form of liposomes obtained in Example 2 of patent application ES-A-2231037 4 and 11 days after the infection of the mice by means of aerosol.

4) Subcutaneously inoculated with a dose of $2\times10^6$ colony forming units of the BCG Danish strain (Statens Serum Institute, Denmark) 4 days after the infection of the mice by means of aerosol.

The virulent strain of *Mycobacterium tuberculosis* (H37Rv Pasteur), which was cultivated in Proskauer-Beck medium until a mid-log phase, was used for the infection and it was stored in aliquots of 1 ml at a temperature of −70° C. until its use.

The mice were aerosol-infected with said virulent strain at the beginning of the experiment by means of placing them in a Middlebrook aerosol infection apparatus which provided an inoculum of approximately 10-50 viable bacilli in the lungs of the mice.

The number of viable bacilli in the lungs and in the spleen was determined 21 days after the aerosol infection of the animals (week 3 of the experiment) incubating serial dilutions of lung and spleen homogenates in Middlebrook 7H11 agar for 4 weeks at 37° C. The lung and spleen were homogenized in the presence of 1 ml of twice-distilled water.

The results of Table I express the logarithm of the colony forming units (CFU) per ml which have been identified in the lung:

TABLE I

| Group of mice | Vaccine | $Log_{10}CFU/ml$ |
|---|---|---|
| 1 | None (Control group) | 6.23 ± 0.23 |
| 2 | Immunotherapeutic agent in the form of liposomes 1 dose | 5.83 ± 0.22 |
| 3 | Immunotherapeutic agent in the form of liposomes 2 doses | 5.49 ± 0.56 |
| 4 | Conventional BCG vaccine | 6.14 ± 0.20 |

In the lung, the differences between the result of the group of mice that have been treated with the liposome-encapsulated immunotherapeutic agent and those which have not are statistically significant.

It can be observed that in the lung of the group of mice vaccinated with the liposome-encapsulated immunotherapeutic agent a smaller number of viable bacilli than in the lung of the mice of the other groups is detected.

The results of Table II express the logarithm of the colony forming units (CFU) per ml which have been identified in the spleen:

TABLE II

| Group of mice | Vaccine | $Log_{10}CFU/ml$ |
|---|---|---|
| 1 | None (Control group) | 4.34 ± 0.62 |
| 2 | Immunotherapeutic agent in the form of liposomes 1 dose | 3.99 ± 0.66 |
| 3 | Immunotherapeutic agent in the form of liposomes 2 doses | 3.30 ± 2.29 |
| 4 | Conventional BCG vaccine | 4.46 ± 0.68 |

Though there are no statistically significant differences in the spleen, it should be pointed out that the administration of the immunotherapeutic agent in the form of liposomes reduced the *bacillus* concentration to the point that the *bacillus* population in the group treated with two doses of the agent was eradicated (CFU=0) in 4 out of 14 cases, hence the high standard deviation detected.

Therefore, the primary prophylaxis with the immunotherapeutic agent based on cell wall fragments of a virulent strain of MTB-C protects against recent infections caused by *M. tuberculosis* because it generates a protective response, in contrast with the lower efficacy demonstrated by the conventional BCG vaccine.

Despite the fact that the conventional BCG vaccine and the immunotherapeutic agent containing cell wall fragments have a substantially identical immunoprotective behavior when they are administered as prophylactic vaccine sufficiently in advance with respect to infection, as disclosed in patent application WO-A-2008/053055, the results of Example 1 show the difference between both drugs when they are used in the primary prophylaxis of tuberculosis for preventing infection due to contacts in individuals who are not infected but have been exposed to the contagion.

The invention claimed is:

1. A method for the primary prophylaxis of tuberculosis comprising administering to an individual who is exposed to tuberculosis contagion and who has not tested positive in a tuberculin skin test an immunotherapeutic agent comprising cell wall fragments of a virulent strain of *Mycobacterium tuberculosis*-complex (MTB-C), wherein said agent is obtainable by a method comprising the following steps:

culturing the virulent strain of MTB-C for a time period equal to or greater than three weeks and subsequently homogenizing the cell culture in the presence of a nonionic surfactant.

2. The method according to claim 1, wherein the culture time period is between 3 and 4 weeks.

3. The method according to claim 1, wherein the nonionic surfactant is selected from the group consisting of the ethoxylated alkylphenols, ethoxylated sorbitan esters, and mixtures thereof.

4. The method according to claim 3, wherein the nonionic surfactant is selected from the group of ethoxylated octylphenols.

5. The method according to claim 4, wherein the nonionic surfactant is selected from ethoxylated octylphenols with an ethylene oxide content comprised between 7 and 8 moles.

6. The method according to claim 1, wherein the homogenization is performed in a neutral pH buffered medium.

7. The method according to claim 1, wherein the method for obtaining the immunotherapeutic agent further comprises the following steps:
separating the non-fragmented cells and the solubilized components by means of centrifugation,
subjecting the fraction of cell wall fragments to chemical or physical treatment to inactivate the eventual virulent strain cells that it eventually contains, and
drying the obtained immunotherapeutic agent by means of lyophilization.

8. The method according to claim 1, wherein the drug is in the form of liposomes.

9. The method according to claim 1, wherein the drug is administered in the form of a single dose or of several doses.

10. The method according to claim 9, wherein the drug is administered in two doses.

11. The method according to claim 10 wherein the doses are administered separated by a time period of between 1 and 5 weeks.

12. The method according to claim 1, wherein the drug is administered in combination with other drugs suitable for the primary prophylaxis of tuberculosis.

13. The method according to claim 12, wherein the drug is administered in combination with the isoniazid.

14. The method according to claim 2, wherein the nonionic surfactant is selected from the group consisting of the ethoxylated alkylphenols, ethoxylated sorbitan esters, and mixtures thereof.

* * * * *